United States Patent [19]
Flatt et al.

[11] Patent Number: 6,060,306
[45] Date of Patent: May 9, 2000

[54] APPARATUS AND METHOD FOR STERILIZING, SEEDING, CULTURING, STORING, SHIPPING AND TESTING REPLACEMENT CARTILAGE TISSUE CONSTRUCTS

[75] Inventors: James H. Flatt, Del Mar; Mark A. Applegate, San Diego; Alvin Peterson, Jamul, all of Calif.

[73] Assignee: Advanced Tissue Sciences, Inc., La Jolla, Calif.

[21] Appl. No.: 08/912,948

[22] Filed: Aug. 14, 1997

Related U.S. Application Data

[63] Continuation of application No. 08/486,185, Jun. 7, 1995, abandoned.

[51] Int. Cl.[7] .............................. C12M 3/00; C12N 5/00
[52] U.S. Cl. .................................... 435/297.2; 435/286.5; 435/401
[58] Field of Search .................................. 623/1, 11, 16, 623/66; 424/422–425; 435/240.241, 240.23, 284, 285, 301, 395, 398, 389, 401, 402, 297.2, 297.4, 286.5

[56] References Cited

U.S. PATENT DOCUMENTS

| | | |
|---|---|---|
| 3,734,851 | 5/1973 | Matsumura . |
| 3,883,393 | 5/1975 | Knazek et al. ........................ 195/1.8 |
| 4,201,845 | 5/1980 | Feder et al. . |
| 4,417,861 | 11/1983 | Tolbert . |
| 4,639,422 | 1/1987 | Geimer et al. . |
| 4,762,794 | 8/1988 | Nees . |
| 4,804,628 | 2/1989 | Cracauer et al. ..................... 435/240 |
| 4,988,623 | 1/1991 | Schwarz et al. . |
| 5,026,650 | 6/1991 | Schwarz et al. . |
| 5,043,260 | 8/1991 | Jauregul . |
| 5,068,195 | 11/1991 | Howell et al. . |
| 5,081,035 | 1/1992 | Halberstadt et al. . |
| 5,153,131 | 10/1992 | Wolf et al. . |
| 5,153,132 | 10/1992 | Goodwin et al. . |
| 5,153,133 | 10/1992 | Schwarz et al. . |
| 5,155,034 | 10/1992 | Wolf et al. . |
| 5,155,035 | 10/1992 | Schwarz et al. . |
| 5,230,693 | 7/1993 | Williams et al. . |
| 5,266,480 | 11/1993 | Naughton et al. . |
| 5,308,764 | 5/1994 | Goodwin et al. . |
| 5,376,110 | 12/1994 | Tu et al. . |
| 5,792,603 | 8/1998 | Dunkelman et al. . |

FOREIGN PATENT DOCUMENTS

| | | |
|---|---|---|
| WO 90/13639 | 11/1990 | WIPO . |
| WO 92/11355 | 7/1992 | WIPO . |
| WO 93/01843 | 2/1993 | WIPO . |
| WO 93/12805 | 7/1993 | WIPO . |
| WO 93/18132 | 9/1993 | WIPO . |
| WO 94/25584 | 11/1994 | WIPO . |

OTHER PUBLICATIONS

Eskin et al. 'Behavior of Endothelial Cells Cultured . . . ' Artificial Organs. vol. 7, No. 1 (1983), pp. 31–37.
Atikinson et al.; *Biochemical Engineering and Biotechnology Handbook*; pp. 476–487 (1991).
Halberstadt et al., "The In Vitro Growth of a Three–Dimensional Human Dermal Replacement Using a Single–Pass Perfusion System," *Biotechnology and Bioengineering* 43:740–746 (1994).

*Primary Examiner*—William H. Beisner
*Attorney, Agent, or Firm*—Pennie & Edmonds LLP

[57] ABSTRACT

An apparatus and method for sterilizing, seeding, culturing, storing, shipping, and testing cartilage constructs is disclosed. The apparatus generally includes a treatment chamber and a means for varying the fluid flow and pressure within the treatment chamber during seeding and culturing. The application of pressure to the cartilage construct improves both the uniformity of seeding throughout the construct and facilitates the flow of nutrients to and removal of waste products from cells embedded in the construct. In this manner, a tissue-engineered cartilage construct with cells and their fibers oriented in a manner which is more likely to possess long term dimensional stability and the patency of cartilage with normal physiologic function may be formed.

43 Claims, 7 Drawing Sheets

APPARATUS AND METHOD FOR STERILIZING, SEEDING, CULTURING, STORING, SHIPPING AND TESTING REPLACEMENT CARTILAGE TISSUE CONSTRUCTS

This is a continuation of application Ser. No. 08/486,185, filed Jun. 7, 1995, now abandoned.

BACKGROUND OF THE INVENTION

1. Technical Field

The present invention relates to the sterilization, seeding, culturing, storing, shipping, and testing of replacement cartilage tissue constructs. Specifically, the present invention relates to an apparatus and method for sterilizing cartilage constructs and then seeding and culturing the constructs with viable mammalian cells, resulting in constructs more likely to display the biochemical, physical, and structural properties of native cartilage tissue.

2. Discussion of the Related Art

Articular cartilage is responsible for providing moveable joints with the ability to perform smooth gliding motions. Articular cartilage consists of highly specialized cells (chondrocytes) surrounded by a dense extracellular matrix (ECM) consisting primarily of type II collagen, proteoglycan, and water. Resistance of the ECM to water flow gives cartilage the ability to disperse high joint loads by absorbing shock and minimizing stress on subchondral bone.

However, fully matured cartilage has limited ability for self renewal and repair. Thus, tissue damage from, for example, trauma or degenerative joint disease, can lead to continuous destruction of cartilage and eventually osteoarthritis. Due to the large number of orthopedic surgeries that are required to treat damaged cartilage, there is great demand for replacement cartilaginous tissue.

The seeding and culturing of tissue for use in replacement therapy is known in the art. For example, U.S. Pat. No. 5,266,480 to Naughton et al. discloses the establishment of a three dimensional matrix, seeding of the matrix with desired cells, and maintenance of the culture to provide a variety of three-dimensional tissues suitable for use in different applications.

Historically, the seeding and culturing of tissue has taken place in a static environment such as a Petri or culture dish. However, there are disadvantages to seeding and culturing tissue in such an environment. First, achieving acceptable seeding of cells throughout the thick cartilage tissue construct without forced convection, as exists in a static system, is difficult. Second, maintaining an adequate supply of nutrients to chondrocyte or related cells throughout a replacement cartilage tissue construct is difficult in a static system given the relative thickness (approximately 2–5 mm) and density of the microporous construct. Moreover, the density of the construct increases significantly during the seeding and culturing process as cells proliferate and fill interstitial spaces. Thus, the lack of circulation of nutrients in a static system results in a slow and ineffective seeding and culturing process.

In contrast, cells which are seeded and cultured in a dynamic environment are more likely to tolerate the physiological conditions which exist in the human body once implanted. This is because a culturing condition of periodic or continuous fluid flow and pressure more closely resembles the conditions under which articular chondrocyte cells are cultured in the human body, which will result in the formation of a tissue-engineered cartilage construct which possesses physical and biochemical properties that are similar to native cartilage. Thus, there exists a need for a dynamic environment in which to seed and culture replacement cartilage tissue constructs and other prosthetic devices.

SUMMARY OF THE INVENTION

It is therefore an object of the invention to stimulate the production of replacement cartilage tissue constructs which display the critical biochemical, physical, and structural properties of native human cartilage tissue by seeding and culturing the tissue in a dynamic environment.

It is a further object of the invention to provide a precise mechanical device with a minimum of moving parts to provide such an environment.

It is yet a further object of the invention to provide a closed system free from contamination for sterilizing, seeding, culturing, storing, shipping, and testing replacement cartilage tissue constructs.

In accordance with the present invention, there is provided an apparatus and method for sterilizing, seeding, culturing, storing, shipping, and testing cartilage tissue constructs. Specifically, the present invention is an apparatus and method for seeding and culturing constructs with mammalian cells, such as chondrocytes, resulting in tissue-engineered cartilage constructs populated with viable mammalian cells.

The apparatus according to the present invention comprises a fluid reservoir, at least one construct treatment chamber, and a pressure source for applying pressure to the construct housed in the treatment chamber. Applying pressure to the construct located within the treatment chamber during seeding and culturing results in a cartilage construct with cells and their fibers oriented so as to more likely tolerate the physiological conditions found in the human body. In this manner, the invention advantageously utilizes a mechanically non-complex apparatus to create a dynamic environment in which to seed and culture tissue-engineered cartilage constructs or other implantable devices.

BRIEF DESCRIPTION OF THE DRAWINGS

These and other features, aspects, and advantages of the present invention will become more readily apparent from the following detailed description, which should be read in conjunction with the accompanying drawings in which:

FIGS. 1A–1E illustrate an apparatus according to the present invention for sterilizing, seeding, culturing, storing, shipping, and testing a prosthesis in which a piston and cylinder arrangement is utilized, wherein FIGS. 1B and 1C illustrate fluid flow during use and FIGS. 1D and 1E illustrate alternative embodiments of a treatment chamber;

FIGS. 3A–3D illustrate an alternative exemplary embodiment of the present invention for sterilizing, seeding, culturing, storing, shipping, and testing a prosthesis in which a bellows is utilized, wherein FIG. 3B is a cross-sectional view and FIGS. 3C and 3D illustrate alternative embodiments of a frame for securing cartilage constructs;

DETAILED DESCRIPTION OF THE INVENTION

The following embodiments of the present invention will be described in the context of an apparatus and method for sterilizing, seeding, culturing, storing, shipping, and testing cartilage constructs, although those skilled in the art will recognize that the disclosed methods and structures are readily adaptable for broader application. Note that whenever the same reference numeral is repeated with respect to different figures, it refers to the corresponding structure in each such figure.

FIGS. 1A–1E disclose a system for sterilizing, seeding, culturing, storing, shipping, and testing cartilage constructs. According to a preferred embodiment of the invention, this system primarily comprises a treatment chamber 10, a pair of pistons 12 and 14, and a media reservoir 26 communicating with the treatment chamber.

Figure 1A:
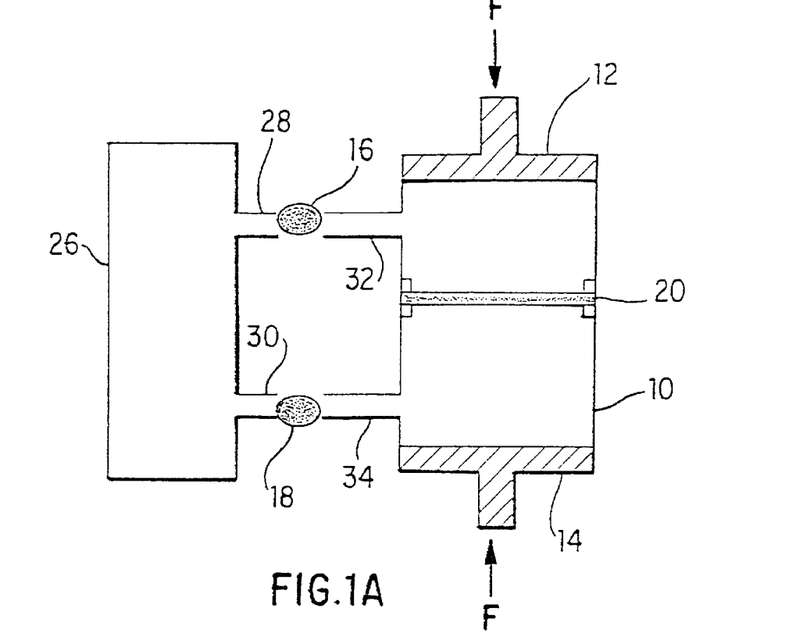

Media reservoir 26 is used to store fluid for the system. Illustrative suitable reservoirs are the Gibco-BRL 1L media bag or any rigid container capable of sterilization. Reservoir 26 may include a one way sterile filter so as to provide a direct source of sterile gas to the fluid within the system or, alternatively, may include gas-permeable tubing or membranes comprised of a material such as silicone or Teflon so as to provide an indirect source of sterile gas to the system via diffusion. Examples of fluid which may be used in the system include, but are not limited to, sterilizing fluid, tanning fluid, fluid containing cells, or fluid containing a culture medium. It is to be understood that during testing, seeding, and culturing in a preferred embodiment, the fluid may be advantageously kept at human body temperature, and may be composed of a fluid which approximates the viscosity of human blood or other human bodily fluids.

The fluid contained in reservoir 26 is retrieved through fluid lines 28 and 30 into treatment chamber 10 through the actions of pistons 12 and 14, which, as is discussed below, control both the flow and pressure of the fluid within the system. Fluid lines 28 and 30, as well as all other fluid lines in the system, may be made of any type of stainless steel tubing or medical grade, sterilizable, durable, plastic tubing preferably comprised of a gas-permeable material such as silicone which is suitable for transporting the fluid in use.

Treatment chamber 10 preferably may be composed of any biocompatible, rigid material capable of being sterilized such as Teflon, polycarbonate, PVC, or stainless steel. Treatment chamber 10 may be a single piece of material or, as is discussed in more detail below, may be comprised of two sections which are secured and made leak proof through any standard means such as inner and outer threads, an o-ring seated in an annular groove, a clamp, or bonding agents. In order to view cartilage construct 20 within treatment chamber 10, a viewing port may be placed at any point on the chamber, or alternatively, the chamber may be made of an optically clear material such as polycarbonate or PVC. Ports 32 and 34 of treatment chamber 10 allow for the perfusion and/or circulation of fluid into and through the chamber. Ports 32 and 34 are also used to attach treatment chamber 10 to fluid lines 28 and 30 respectively. Valves 16 and 18 are disposed in fluid lines 28 and 30 to control flow therethrough. Valves 16 and 18 can be any valve that may be mechanically, pneumatically, and/or electronically opened and closed at a variety of intervals, and preferably non-invasive to minimize the potential for contamination of the cell culture medium.

As mentioned, treatment chamber 10 may be used to house a cartilage construct 20. Cartilage construct 20 may illustratively consist of any knitted, braided, woven, felted, or synthesized material that is bioresorbable and/or biocompatible, as well as any native cartilage material which will support appropriate cells. Treatment chamber 10 may be made any size so as to hold a cartilage construct 20 of any length or diameter. This is advantageous, as the system may be used to sterilize, seed, culture, store, ship, and test constructs of any size.

Figure 1B:
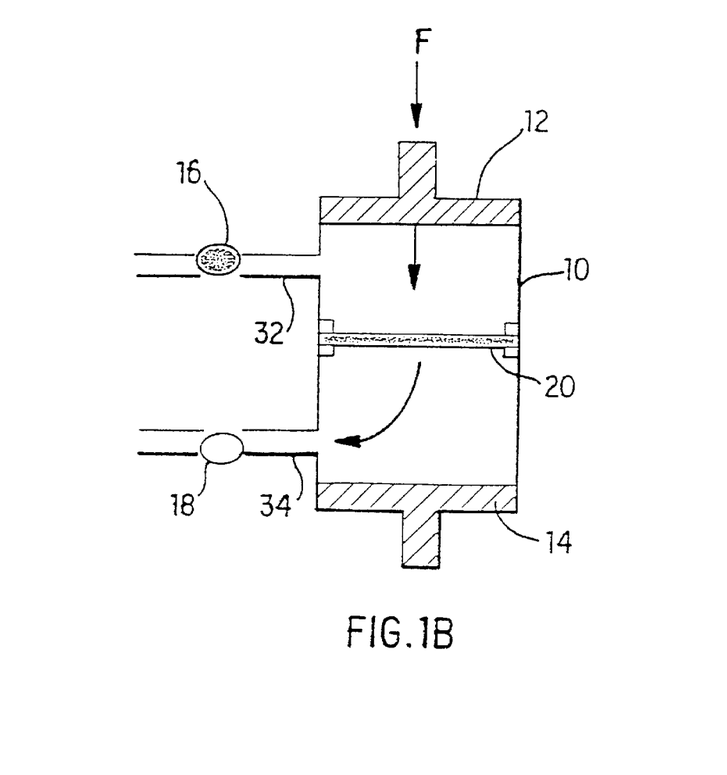
Figure 1C:
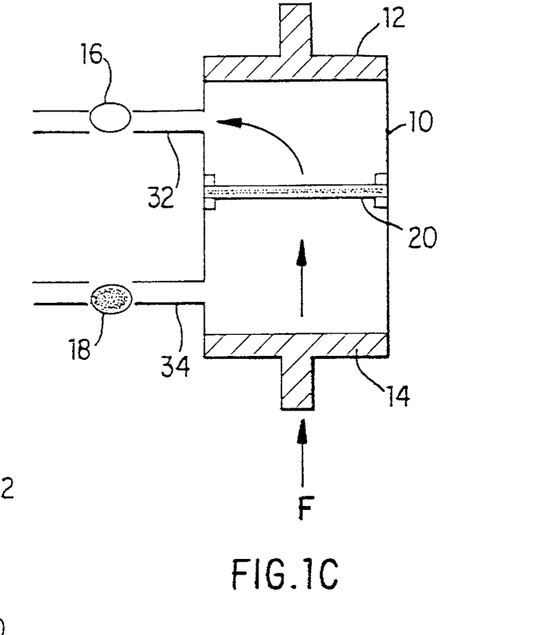
Figure 1D:
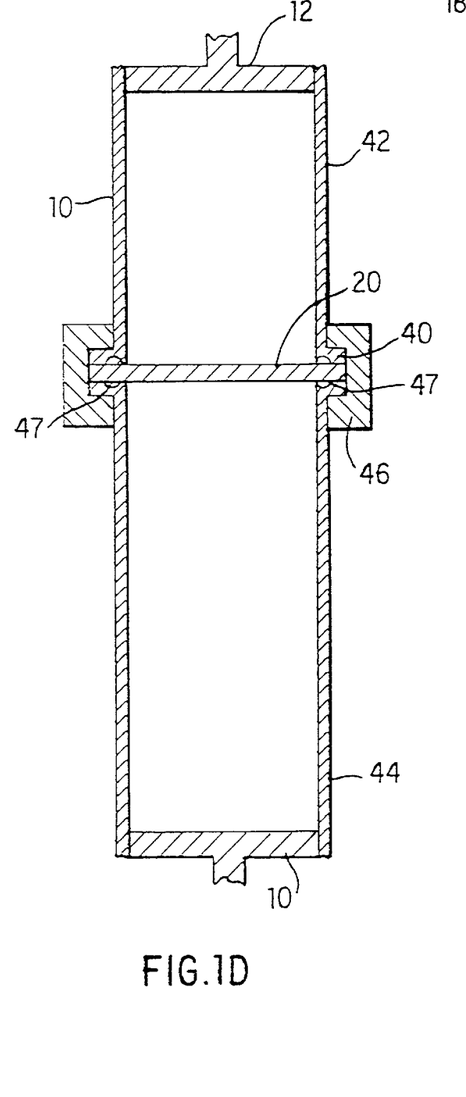

As shown in FIG. 1D, treatment chamber 10 may contain ferrules or flanges 40 which allow sections 42 and 44 of a two-piece chamber to be secured together by clamp 46. Clamp 46 may be any suitable clamp such as a sanitary clamp. The connection between sections 42 and 44 may be made leak proof by a gasket or an o-ring, which can be seated in the annular grooves 47 of flanges 46 found in each section.

In a preferred embodiment of the present invention, construct 20 is secured within treatment chamber 10 so as to form a seal with the chamber around the periphery of the construct. Such a seal requires fluid flowing through chamber 10 to flow through construct 20, thus creating a pressure drop at the construct which creates an advantageous seeding and culturing environment. By controlling the flow through the chamber (by pumps, pistons or other means), the pressure drop is used to create alternating periods of higher and lower pressure acting on one or both sides of the construct. In an alternative embodiment in which less fluid flow through construct 20 is desired, construct 20 may be secured within chamber 10 in a manner which does not form a seal, and thus, which allows some fluid to flow around construct 20. Additionally, the necessary effects may be obtainable in a static chamber, without continuous flow. In such an embodiment, the construct is placed within a chamber containing a volume of desired media. The chamber is intermittently pressurized as is appropriate for the particular construct, for example by application of a piston or other means. The construct is thus exposed to alternating higher and lower pressures which tends to cause media to move in and out of the porous construct structure.

Thus, as is shown in FIG. 1D, construct 20 may be made so as to fit securely in between sections 42 and 44 so as to hold the construct 20 firmly in place in chamber 10 and create a seal between sections 42 and 44 during treatment. Construct 20 may also be secured in place in between two screens or other matrix members which may also be secured in place between sections 42 and 44 so as to create a seal. The screens or matrix members may also be attached by any mechanical means within chamber 10. However, one skilled in the art will understand that any structure which allows for the retention of construct 20 in chamber 10 may be used.

Figure 1E:
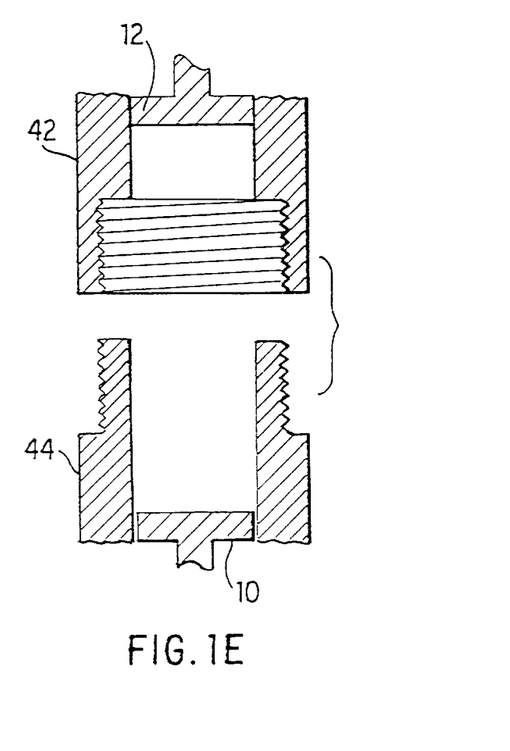

An alternative embodiment of a two-piece chamber is disclosed in FIG. 1E in which sections 42 and 44 are threaded together. Like the embodiment of FIG. 1D, construct 20 may be secured in place between the two sections 42 and 44 so as to create a seal or, alternatively, construct 20 may be secured in place in between two screens or matrix members which may be secured in place between sections 42 and 44.

As mentioned, pistons 12 and 14 control both the flow and pressure of the fluid within treatment chamber 10. Pistons 12 and 14 are configured and dimensioned so as to create a hermetically sealed chamber 10. Force may be applied to pistons 12 and 14 (as shown by the arrows labeled F) by any well known means, such as an electrically-driven rotating cam, an electromechanical or pneumatic displacement device, or an electrically or pneumatically-driven lever arm. It is to be understood that the force applied to pistons 12 and 14 may be varied so as to provide varying pressure within treatment chamber 10 during use. This is advantageous as the ideal pressure to be applied to the construct will vary with time due to the increasing density of the construct during seeding and culturing. Moreover, the ideal pressure to be applied necessarily depends from the outset on the original thickness of the construct, and may thus vary from treatment to treatment.

FIGS. 1B and 1C particularly point out and illustrate the preferred fluid flow during use. This illustrated fluid flow is preferred for constructs of exceptional thickness or density, especially where avoidance of "sidedness" or a gradient in construct 20 is critical. FIG. 1B shows treatment chamber 10 when valve 16 is closed and a force is applied to piston 12. When piston 12 is moved towards construct 20 so as to shrink the volume of the chamber, all fluid is forced through the construct (as shown by the arrows) and out port 34.

However, as shown in FIG. 1C, once force is applied to piston 14 and valve 18 is closed, fluid is then forced in an opposite direction through construct 20 (as shown by the arrows) and out through open valve 16. Thus, in a preferred embodiment, the piston and valve positions are coordinated such that fluid is forced through construct 20 bidirectionally.

However, it is to be understood that pistons 12 and 14 may be actuated in any order and at any interval. Thus, pistons 12 and 14 may be actuated in an alternating fashion at some predetermined interval, or alternatively, one piston may be actuated for a predetermined period of time followed by actuation of the other piston for a preferably similar period of time. Likewise, both pistons may be actuated simultaneously to simulate intermittent cartilage pressurization without fluid flow similar to that found in the human body.

In this manner, periodic fluid flow and pressurization in treatment chamber 10 is accomplished which resembles the physiological conditions typically encountered by articular cartilage in the human body. These conditions are advantageous as they improve the flow of nutrients to and removal of waste products from cells embedded in the construct. These conditions are also advantageous as they can be detected by living cells attached to construct 20, thus causing the cells to align and configure themselves in a manner more likely to tolerate the physiological conditions found in the human body.

Figure 2A:
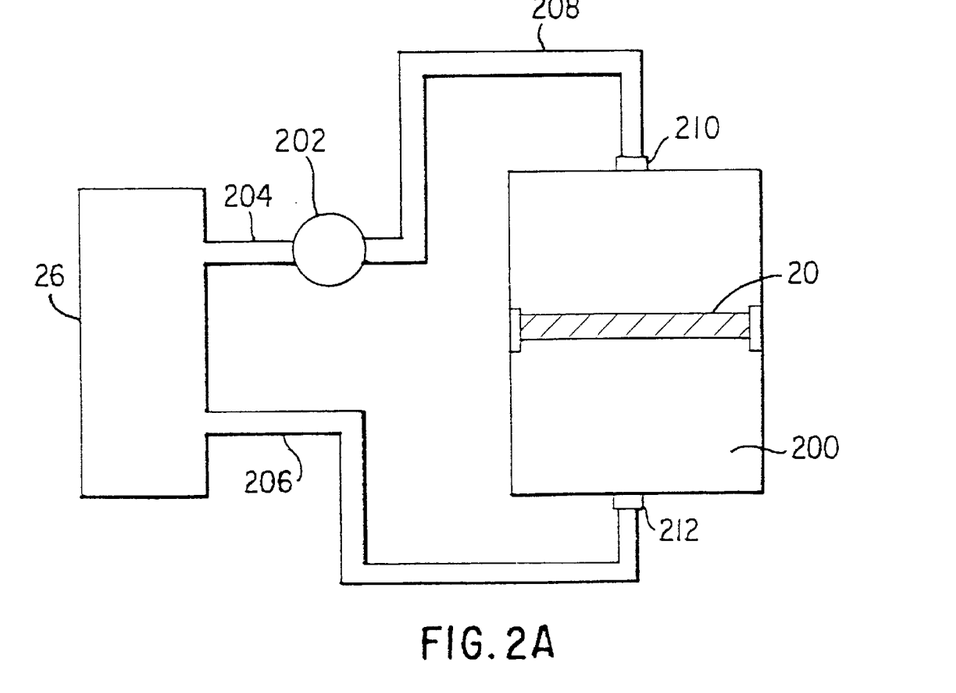
FIGS. 2A–2B illustrate an apparatus according to the present invention for sterilizing, seeding, culturing, storing, shipping, and testing a prosthesis, in which a pump is utilized.
Figure 2B:
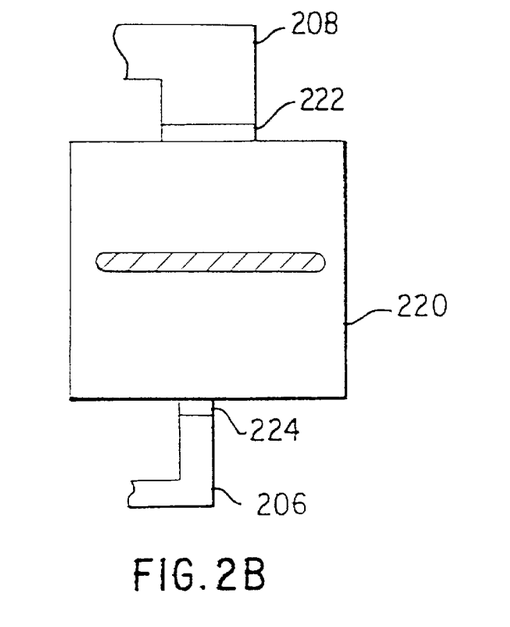

FIGS. 2A–2B disclose an alternative embodiment of a system for sterilizing, seeding, culturing, storing, shipping, and testing cartilage constructs. According to a preferred embodiment of the invention, shown in FIG. 2A, this system primarily comprises a treatment chamber 200, a pump 202, and a media reservoir 26 communicating with the treatment chamber.

Media reservoir 26, and the fluids which it may contain are the same as those disclosed in conjunction with FIGS. 1A–1E. The fluid contained in reservoir 26 may be retrieved through fluid lines 204 and 206 into treatment chamber 200 through the action of pump 202, which, as is discussed below, controls both the flow and pressure of the fluid within the system. Fluid lines 204 and 206, as well as all other fluid lines in the system, may illustratively be made of any type of stainless steel tubing or medical grade, sterilizable, durable tubing preferably comprised of a gas-permeable material such as silicone which is suitable for transporting the fluid in use.

Treatment chamber 200 preferably may be composed of any biocompatible, rigid material capable of being sterilized such as Teflon, polycarbonate, PVC, or stainless steel. Like treatment chamber 10 disclosed in FIGS. 1A–1E, treatment chamber 200 may be a single piece of material or, as is discussed in more detail below, may be comprised of two sections which are secured and made leak proof through any standard means such as inner and outer threads, an o-ring seated in an annular groove, a clamp, or bonding agents. In order to view cartilage constructs within treatment chamber 200, a viewing port may be placed at any point on the chamber, or alternatively, the chamber may be made of an optically clear material such as polycarbonate or PVC. Ports 210 and 212 of treatment chamber 200 allow for the perfusion and/or circulation of fluid into and through the chamber. Ports 210 and 212 are also used to attach treatment chamber 200 to fluid lines 208 and 212 respectively.

Treatment chamber 200 may be used to house cartilage construct 20. Treatment chamber 200 may be made any size so as to hold a cartilage construct 20 of any length or diameter. This is advantageous, as the system may be used to sterilize, seed, culture, store, ship, and test constructs of any size.

As in the embodiment disclosed in FIGS 1A–1E, construct 20 may preferably be secured within treatment chamber 200 in a manner which forms a seal around the periphery of the construct. Thus, like treatment chamber 10 in FIG. 1D, treatment chamber 200 may contain ferrules or flanges which allow the sections of a two-piece chamber to be secured together by clamp. The connection between the sections may also be made leak proof by a gasket or an o-ring, which can be seated in the annular grooves of the flanges found in each section. Construct 20 may be made so as to fit securely in between the sections of a two-piece treatment chamber 200 so as to hold the construct 20 firmly in place in chamber 200 and create a seal during treatment. Construct 20 may also be secured in place in between two screens or other matrix members which may also be secured in place between the sections so as to create a seal. The screens or matrix members may also be attached by any mechanical means within chamber 200. However, one skilled in the art will understand that any structure which allows for retention of the construct 20 in chamber 200 may be used.

Alternatively, the embodiment of a two-piece chamber disclosed in FIG. 1E in which the sections are threaded together may be used in constructing treatment chamber 200. Like the embodiment of FIG. 1D, construct 20 may be secured in place between the two sections or so as to form a seal which allows for a pressure drop at construct 20 during treatment. Alternatively, construct 20 may be secured in place in between two screens or matrix members which may be secured in place between the threaded sections.

As mentioned, pump 202 controls both the flow and pressure of the fluid within treatment chamber 200. Pump 202 may preferably be any reversible pump capable of providing bidirectional pulsatile or continuous pressure fluid flow in the system. Examples of such pumps include but are not limited to low flow pumps, invasive pumps such as a lobe-type pump, or non-invasive pumps such as a peristaltic pump. Alternatively, pump 202 may be comprised of two one way pumps situated so as to provide bi-directional fluid flow within the system.

Thus, illustratively, when pump 202 is operating so as to force fluid from reservoir 26 to fluid line 204, and subsequently from fluid line 208 into chamber 200, fluid is forced through the construct from port 210 to port 212. However, once pump 202 is operated so as to provide fluid flow in the opposite direction, fluid is then forced in an opposite direction through construct 20 from port 212 to port 210. Thus, in a preferred embodiment, pump 202 is operated such that fluid is forced through construct 20 bidirectionally.

It is to be understood that the pressure from pump 202 may be varied during use so as to provide varying pressure within treatment chamber 200. Moreover, it is to be understood that pump 202 may be operated bidirectionally in any manner and at any interval. Thus, pump 202 may be operated so as to provide bidirectional fluid flow in an alternating fashion at some predetermined interval. Alternatively, pump 202 may provide fluid flow in one direction for a predetermined period of time followed by fluid flow in the opposite direction for a preferably similar period of time. Moreover, it is to be understood that, alternatively, one skilled in the art could devise a suitable valving system (e.g., through the use of a rotating valve) that could also provide chamber 200 with a bidirectional fluid flow across construct 20.

Alternatively, treatment chamber 220 shown in FIG. 2B may be used in conjunction with pump 202. In this embodiment, port 222 is larger than orifice 224 of treatment chamber 220. In addition, in this embodiment pump 202 would preferably only pump fluid in one direction through chamber 220, that is from fluid line 208 and port 222 to orifice 224 and fluid line 206, so that a pressure drop is created at orifice 224 and the pressure within chamber 220 is elevated. In this manner, construct 20, which may be either free floating within chamber 220 as shown, loosely secured in the middle of chamber 220, or secured so as to create a seal or a partial seal within the chamber, will experience periodic fluid flow and pressurization in treatment chamber 220 which resembles the physiological conditions typically encountered by articular cartilage in the human body.

FIGS. 3A–3D disclose an alternative embodiment of the invention for sterilizing, seeding, culturing, storing, shipping, and testing cartilage constructs. According to this alternative embodiment of the invention, the system primarily comprises a bellows 50 and a fluid reservoir 26.

Fluid reservoir 26 and the fluids which it may contain are described in detail in conjunction with FIGS. 1A–1E. In the system of FIGS. 3A–3D, the fluid contained in reservoir 26 is retrieved through fluid line 56 by the action of bellows 50. In a preferred embodiment, bellows 50 may be comprised of a hard-sided blow molded collapsible bellows cassette. However, one skilled in the art will understand that other types of bellows which include at least one rigid surface and a flexible edge may be used. Bellows 50 may also include an external pull ring 60 for easy expansion, and may further include a sealable slit 62 along the collapsible side wall so as to place a construct 20 within the bellows for treatment. However, it is to be understood that sealable slit 62 may be placed at any location on bellows 50.

Cartilage construct 20 may be mounted in the center of bellows 50 for treatment. As in the previously discussed embodiments, construct 20 may preferably be mounted within bellows 50 so as to form a sealed barrier in the bellows. One method of mounting a circular-shaped construct 20 in bellows 50 so as to form a seal is through the use of a rectangular-shaped frame 66, shown in FIG. 3C, configured and dimensioned to support a circular construct 20. Alternatively, frame 67 may be used which allows for treatment of multiple constructs at one time. However, although frame 67 illustrates six holes for treating six constructs, it is to be understood that frames 66 and 67 may be configured and dimensioned so as to treat any number of constructs of any shape.

Construct 20 may be attached to frames 66 and 67 by any means such as sutures, staples, c-clips, or may be sandwiched between two opposable interlocking frames 66 or 67. Frames 66 and 67 may be comprised of any material such as plastic or elastomeric polymers including, but not limited to, fluorinated polymers, polycarbonate, ester- or vinyl-based polymers and polyolefin polymers, and may be attached or anchored within bellows 50 through pins or other mechanical means which preferably allow for the formation of a tight seal between the frame and the walls of the bellows. However, one skilled in the art will understand that any structure which allows for the retention of construct 20 within bellows 50 may be used. For example, as mentioned in conjunction with FIGS. 1A–1E, in a lesser preferred embodiment, construct 20 may be attached in a manner that does not form a seal, and thus, which allows some fluid to flow around and not through construct 20.

Figure 3A:
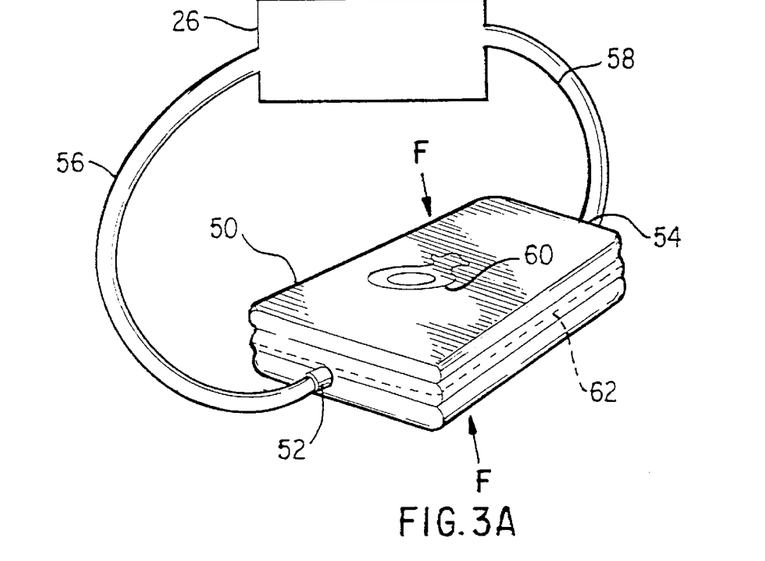
Figure 3B:
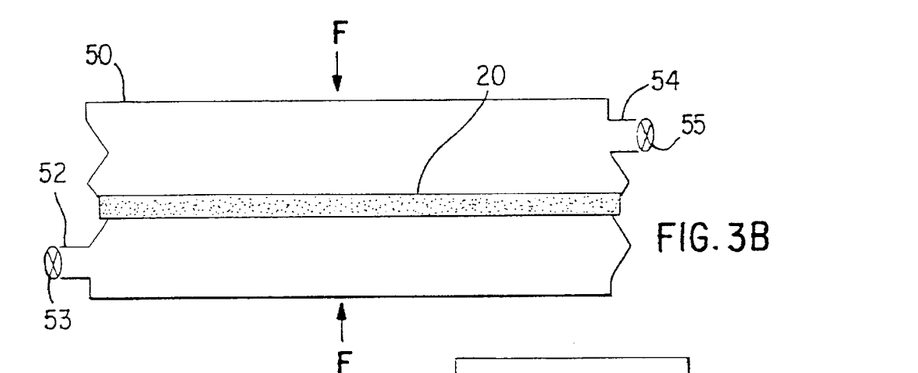
Figure 3C:
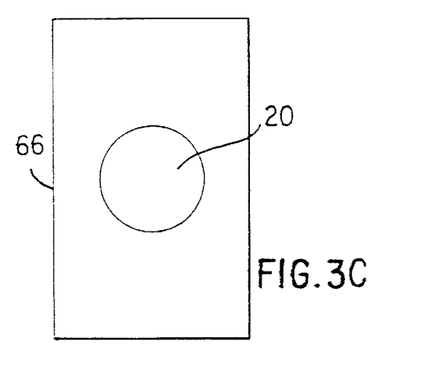
Figure 3D:
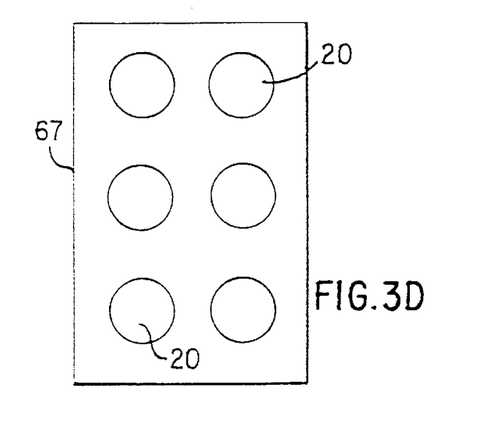

As shown by the arrows in FIGS. 3A and 3B, a mechanical force may be applied to bellows 50 so as to apply pressure to construct 20 and force fluid through the bellows. One skilled in the art will understand that any type of mechanical force, such as a an electromechanical or pneumatic displacement device or an electrically or pneumatically-driven lever arm, may be used to place a force on the bellows. In a preferred embodiment of the invention, bellows 50 is alternately expanded and contracted so as to force fluid through the bellows as well as through construct 20 mounted within the bellows. Expanding and contracting bellows 50 also acts to place a varying pressure on construct 20. Ports 52 and 54 allow for the perfusion and/or circulation of fluid into and through bellows 50. Ports 52 and 54 are also used to attach bellows 50 to fluid lines 56 and 58 respectively. Fluid line 58 connects bellows 50 back to reservoir 26 so as to create a closed system.

Ports 52 and 54 preferably may include valves 53 and 55 as shown in FIG. 3B so as to assure that fluid may be forced to flow bidirectionally through bellows 50. Valves 53 and 55 can be any valve that may be mechanically, pneumatically and/or electronically opened and closed at a variety of intervals, and preferably non-invasive to minimize the potential for contamination of the cell culture medium.

Thus, the opening and closing of valves 53 and 55 may be coordinated so that one valve is opened and one valve is closed when the bellows is expanded, and then, when the bellows is contracted, the opened valve is closed and the closed valve is opened. This may be followed on the next expansion and contraction of the bellows by the valves being opened and closed in an opposite manner so that fluid is forced in the opposite direction through bellows 50.

Illustratively, when bellows 50 is expanded by an outside force, fluid could be drawn from fluid reservoir 26 from opened valve 53 into bellows 50 until the bellows is filled with fluid and is in a fully expanded state. During expansion of bellows 50, closed valve 55 will ensure that no fluid is drawn from fluid line 58. Once a positive pressure is applied to bellows 50, the fluid contained in the bellows is forced through construct 20, out of the bellows, and through now opened valve 55 back to reservoir 26. When fluid is forced out of bellows 50, the now closed valve 53 located at port 52 will ensure that no fluid is forced back into fluid line 56. This may be followed on the next expansion and contraction of bellows 50 by the opening and closing of the valves in an opposite manner so that bidirectional fluid flow is created.

However, in a lesser preferred embodiment, simple check valves may be used at ports 52 and 54 so that a unidirectional fluid flow through bellows 50 may be instituted.

Thus, like the system of FIGS. 1A–1E, fluid flow and pressurization is accomplished during seeding, culturing, and testing which closely resembles the physiological conditions found in the human body.

Figure 4:
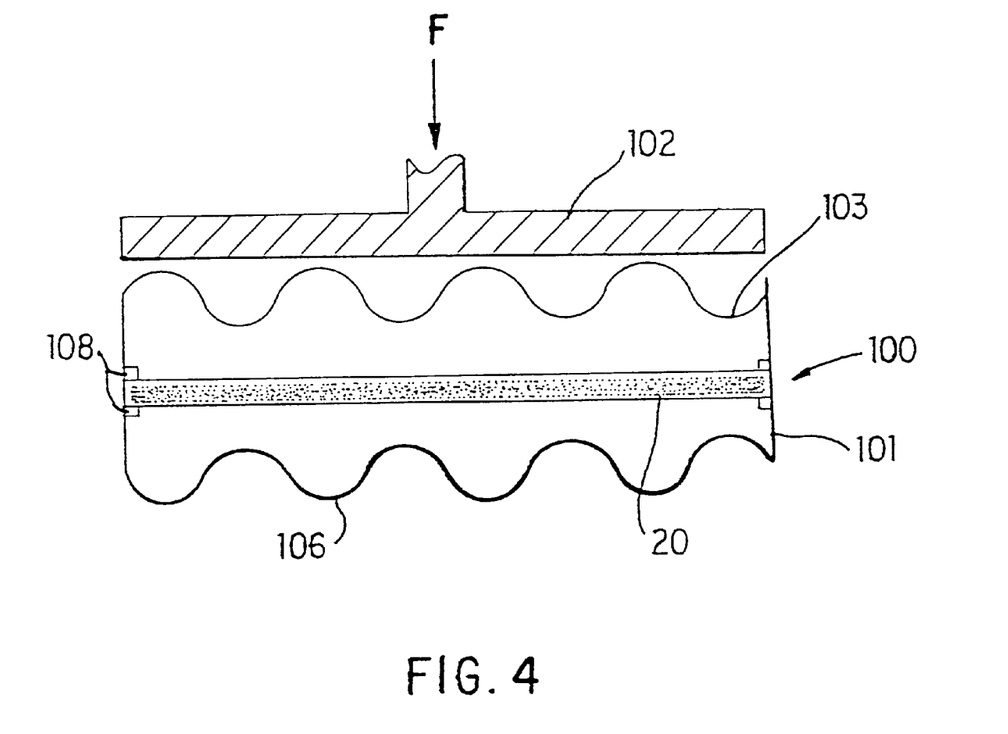
FIG. 4 illustrates another alternative exemplary embodiment of the present invention for sterilizing, seeding, culturing, storing, shipping, and testing a prosthesis in which a pressure plate is utilized.

FIG. 4 discloses yet another alternative embodiment of the invention for sterilizing, seeding, culturing, storing, shipping, and testing cartilage constructs. According to this alternative embodiment of the invention, the system primarily comprises a flexible treatment chamber 100 and at least one pressure plate 102.

Flexible treatment chamber 100 may be used to house any type of suitable fluid, such as those disclosed in conjunction with FIGS. 1A–1E, as well as cartilage construct 20. As shown in FIG. 4, chamber 100 may preferably be comprised of a rigid wall 101 and flexible covers 103 and 106. Rigid wall 101 illustratively may be circular or rectangular in shape. Moreover, cover 106 may be a rigid wall so that wall 101 and cover 106 form a rigid tray. Covers 103 and 106 may be comprised of any biocompatible flexible material, including, but not limited to, plastic or elastomeric polymers such as silicone, fluorinated polymers, ester- or vinyl-based polymers and polyolefin polymers, which preferably allow for the diffusion of gas from the environment into the chamber. Chamber 100 may also include one way inlet and outlet filters so as to provide a direct source of gas to the fluid within the system as well as to provide a method of removing gas from the system. As shown in FIG. 4, during seeding and culturing of construct 20 within treatment chamber 100, pressure plate 102 may be used to apply predetermined levels of pressure (as shown by the arrow labeled F) at predetermined intervals to the chamber and thus, to construct 20 within the chamber. One skilled in the art will understand that any type of mechanical means may be used to apply a force to pressure plate 102.

In an alternative embodiment, a second pressure plate 102 may be used to apply predetermined levels of pressure to the chamber through cover 106, and thus, from the opposite direction of the first pressure plate. Like the actuation of the pistons in FIGS. 1A–1E, in a preferred embodiment, the actuation of the two pressure plates may be coordinated such that fluid is forced through construct 20 bidirectionally.

However, it is to be understood that the two pressure plates 102 may be actuated in any order and at any interval. Thus, the pressure plates may be actuated in an alternating fashion at some predetermined interval, or alternatively, one pressure plate may be actuated for a predetermined period of time followed by actuation of the other pressure plate for a preferably similar period of time. Likewise, both pressure plates may be actuated simultaneously to simulate intermittent cartilage pressurization without fluid flow as is found in the human body.

In this manner, periodic fluid flow and pressurization in treatment chamber 100 is accomplished which resembles the physiological conditions typically encountered by articular cartilage in the human body. These conditions are advantageous as they improve the flow of nutrients to and removal of waste products from cells embedded in the construct. These conditions are also advantageous as they can be detected by living cells attached to construct 20, thus causing the cells to align and configure themselves in a manner more likely to tolerate the physiological conditions found in the human body.

FIG. 4 also discloses a cartilage mount 108 for mounting construct 20 in the center of chamber 100. Cartilage mount 108 may be similar to the frames disclosed in FIGS. 3C and 3D, and may secure construct 20 and be attached to wall 101 in a like manner.

Alternatively, wall 101 may be comprised of two sections like chamber 10 in FIGS. 1D and 1E. In this embodiment, construct 20 may be secured in place in the same manner as disclosed in conjunction with FIGS. 1D and 1E. In this manner, construct 20 may be secured in the center of chamber 100 so as to preferably form a seal during treatment.

In an alternative embodiment, a media reservoir may be connected to chamber 100 in the same manner as media reservoir 26 is connected to bellows 50 in FIG. 2A. Thus, in this alternative embodiment, chamber 100 would include two ports having valves on the opposite sides of the preferable seal created by construct 20 secured within chamber 100. These valves may be operated like those disclosed in conjunction with FIGS. 3A–3D so that bidirectional fluid flow may be created through construct 20.

During treatment, it may be desirable to periodically de-gas chamber 100 so as to improve the effectiveness of the system disclosed in FIG. 4. De-gassing may be accomplished by a variety of methods, such as raising chamber 100 in a vertical orientation and forcing the gas out through a sterile filter located at a predetermined position on the chamber. Finally, like the system disclosed in FIGS. 3A–3D, this system is more amenable to operating at lower pressures than that of the system disclosed in FIGS. 1A–1E.

Figure 5A:
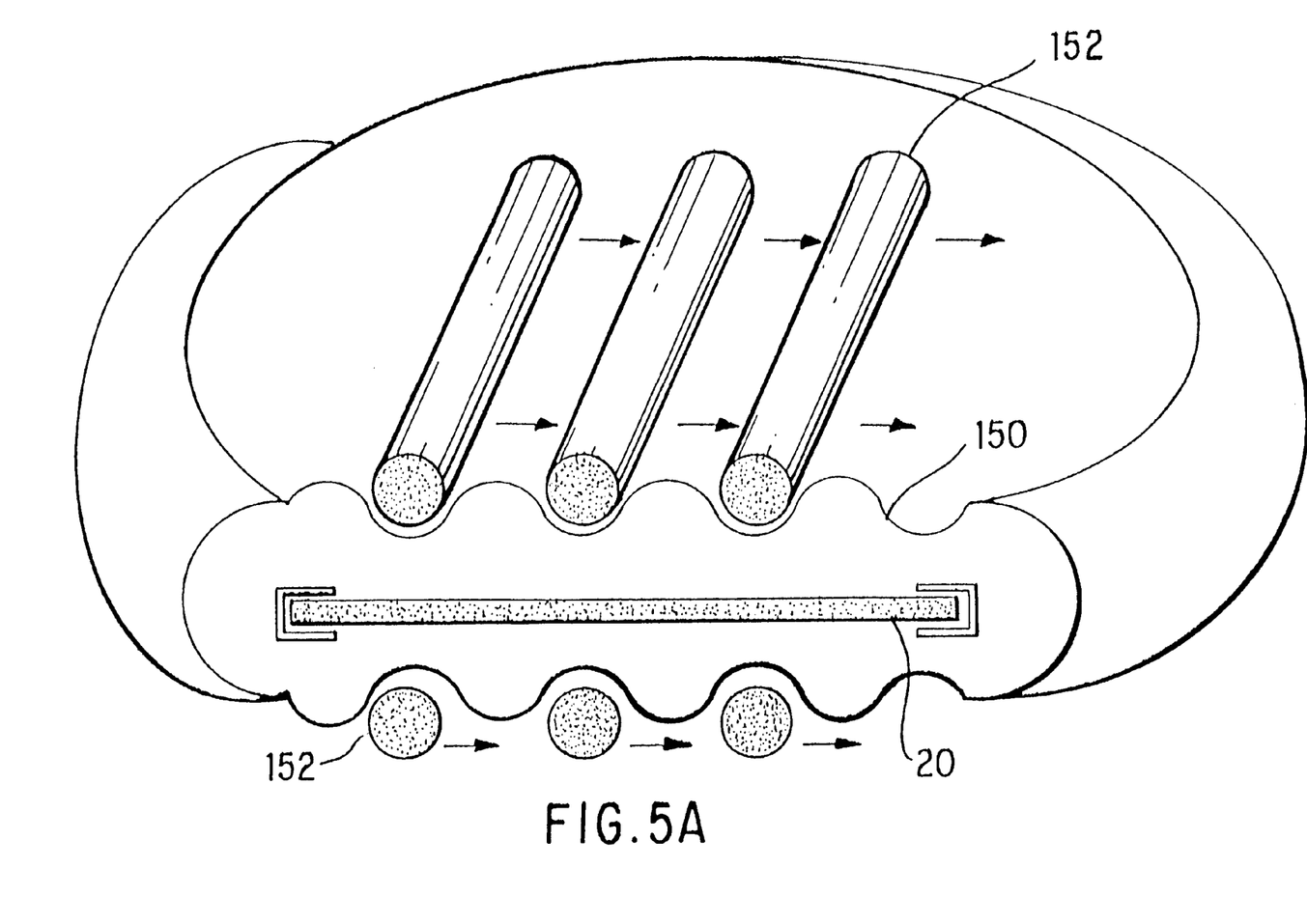
FIGS. 5A–5C illustrate yet another alternative exemplary embodiment of an apparatus according to the present invention for sterilizing, seeding, culturing, storing, shipping, and testing a prosthesis, in which rollers are utilized.
Figure 5B:
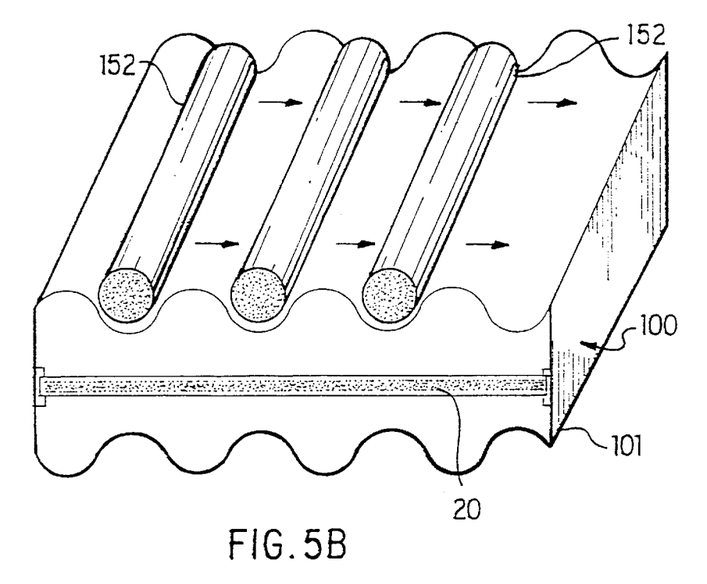
Figure 5C:
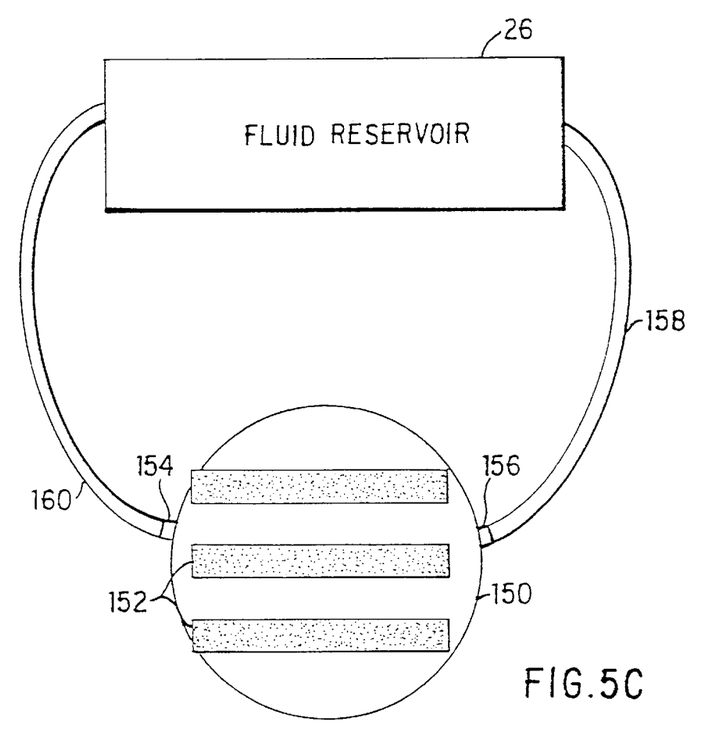

FIGS. 5A–5C disclose yet another alternative embodiment of the invention for sterilizing, seeding, culturing, storing, shipping, and testing cartilage constructs. According to this alternative embodiment of the invention, the system primarily comprises a flexible treatment chamber and at least one roller 152.

Flexible treatment chamber 150 shown in FIG. 5A may be used to house any type of fluid, such as those disclosed in conjunction with FIGS. 1A–1E, as well as a cartilage construct 20. Chamber 150 may preferably be comprised of any biocompatible flexible, gas-permeable material, including, but not limited to, plastic or elastomeric polymers such as silicone, fluorinated polymers, ester- or vinyl-based polymers and polyolefin polymers, which also allows for the diffusion of gas from the environment into the chamber. Chamber 150 may be either sealed so as to create a closed chamber or may include valves, such as timed or check valves, which as shown in FIG. 5C, further link chamber 150 to a media reservoir 26 through lines 158 and 160. Chamber 150 may also include one way inlet and outlet filters so as to provide a direct source of gas to the fluid within the system, and may also include a port for adding or removing fluid media from the chamber.

A construct 20 may be secured in chamber 150 in any manner disclosed above so as to create a seal within chamber 150. If construct 20 is relatively thin, it may not be necessary to positively force flow through the porous structure of the construct. In such a case, high pressures or a peripheral seal may not be required. This is because with a relatively thin construct, convection of the fluid around the construct may provide adequate fluid communication with the cells for seeding, culturing and waste removal, rather than fluid flow through the construct.

As shown in FIG. 5A, during seeding and culturing of construct 20 within treatment chamber 150, rollers 152 may be used to apply pressure to opposite sides of the chamber and thus, to construct 20 within the chamber. Although three rollers are disclosed in FIG. 5A, any number of rollers could be used to apply pressure depending on the size of the construct and the performance of the roller system. As is the case with the system disclosed in FIG. 4, any level of pressure may be applied at any interval. One skilled in the art will understand that any type of mechanical means may be used to move rollers 152 across the surface of chamber 150. In this embodiment, valves may be situated at ends 154 and 156 (shown in FIG. 5C) in a manner which allows for fluid flow in only one direction or bidirectionally through chamber 150 and through construct 20. In this manner, whether or not a fluid reservoir is utilized, fluid flow is created through construct 20 within chamber 150, creating a dynamic seeding and culturing environment.

Alternatively, as shown in FIG. 5B, rollers 152 may be applied to chamber 100 disclosed in FIG. 4A. As mentioned, although chamber 100 may comprise a sealed chamber, in an alternative embodiment, chamber 100 may include valves so as to connect the chamber to media reservoir 26.

It is to be understood that any ports of treatment chamber 10 (in FIGS. 1A–1E), chamber 200 (in FIG. 2A), chamber 220 (in FIG. 2B), bellows 50 (in FIGS. 3A–3B), chamber 100 (in FIGS. 4 and 5B), or chamber 150 (in FIG. 5A) (hereinafter collectively referred to as the "treatment devices") may be sealed in a known manner (e.g., luer locks, o-ring based connectors, or threaded plugs) so as to create a sealed treatment device free from contamination. The sealed treatment devices may be used to sterilize, store, and ship cartilage constructs or other protheses. In particular, prior to placing a sealed treatment device into the systems of FIGS. 1–5, a construct 20 which is secured within the treatment device may be sterilized by some chemical means such as ethylene oxide or peracetic acid, radiation means such as an electron beam or gamma rays, or by steam sterilization. Sealed treatment devices, containing the sterilized cartilage support material, may then be placed back into the systems of FIGS. 1–5 for seeding and culturing and unsealed without contaminating the system or the cartilage construct. Alternatively, the system may be aseptically assembled after sterilization if it is necessary or desirable to use different means to sterilize the treatment devices and the cartilage construct.

Seeding and culturing of the constructs in the systems disclosed in FIGS. 1–5 is generally accomplished by known techniques, with the added benefits and advantages gained from the stress placed upon the construct during seeding or growth steps. Examples of suitable seeding and culturing methods for the growth of three-dimensional cartilage cultures are disclosed in U.S. Pat. No. 5,902,741 entitled "Three-Dimensional Cartilage Cultures" and filed on Jun. 5, 1995, which is incorporated herein by reference. The techniques described in this application for establishing a three-dimensional cartilage construct, inoculating the construct with the desired cells, and maintaining the culture may be readily adapted by a person of ordinary skill in the art for use with the present invention.

Once cartilage construct 20 has reached the desired level of cell density, a preservative may then be pumped into the treatment device. Once the device is filled with the preservative, any ports located on the device may be closed, again creating a sealed device which may then be used to store and/or ship the cultured and preserved cartilage construct. Preferably, the preservative is a cryo-preservative so that the construct may be frozen in the treatment device. In this manner, the sealed treatment devices may be used to sterilize, culture, store, and ship cartilage constructs or other protheses.

Various embodiments of the invention have been described. The descriptions are intended to be illustrative, not limitative. Thus, it will be apparent to those skilled in the art that modifications may be made to the invention as described without departing from the scope of the claims set out below.

We claim:

1. An apparatus for seeding and culturing tissue within fluid media, comprising:

at least one wall defining a seeding and culturing chamber;

a porous substrate disposed within said chamber configured and dimensioned to seal with the chamber, said substrate designed to facilitate three-dimensional tissue growth on said substrate and comprising a three-dimensional framework having interstitial spaces bridgeable by cells;

means for alternatingly creating a pressure differential within the chamber across the substrate to force fluid within the chamber to flow through the substrate; and a support structure located within said chamber configured and dimensioned to support the substrate such that the substrate is sealed with the chamber to direct substantially all fluid flow within the chamber through the substrate.

2. The apparatus of claim 1, wherein said chamber is further defined by at least one piston and said differential pressure creating means comprises means for actuating said at least one piston so as to reduce the volume of the chamber.

3. The apparatus of claim 2, wherein said wall is cylindrically shaped and said chamber is further defined by a first piston and a second piston, said first and second pistons located on opposite ends of said chamber.

4. The apparatus of claim 3, wherein said first and second pistons are simultaneously actuatable to reduce the volume of said chamber, said simultaneous actuation creating pressure across the outside surface of the substrate during seeding and culturing.

5. The apparatus of claim 3, wherein the support structure supporting the substrate seals against the chamber to direct substantially all fluid flow within the chamber through the prosthesis to create a pressure drop.

6. The apparatus of claim 3, wherein said first and second pistons are alternatingly actuatable to reduce the volume of said chamber, said alternating actuation creating bidirectional fluid flow through the substrate during seeding and culturing.

7. The apparatus of claim 6, further comprising:

a first port and a second port located on said cylindrical wall on opposite sides of the sealing support structure;

wherein said first port on the opposite end of said first piston is open when said first piston is actuated so as to reduce the volume of said chamber and said second port on the opposite end of said second piston is open when said second piston is actuated so as to reduce the volume of said chamber; and wherein only one of said first and second ports is open at a time.

8. The apparatus of claim 1, wherein said chamber includes first and second ports to permit flow of fluid therethrough, and wherein said pressure creating means comprises a pump.

9. The apparatus of claim 8, wherein said first port is larger that said second port, and wherein said pump creates fluid flow from said first port to said second port so as to create a pressure drop at said second port and elevate the pressure within the chamber.

10. The apparatus of claim 8, wherein said support structure supporting the substrate seals against the chamber to direct substantially all fluid flow within the chamber through the substrate to create a pressure drop.

11. The apparatus of claim 1, wherein said at least one wall defining a chamber comprises two opposing rigid surfaces attached by a flexible edge surface.

12. The apparatus of claim 11, wherein said pressure creating means comprises means for moving said opposing rigid surfaces towards each other so as to reduce the volume of said chamber.

13. The apparatus of claim 12, wherein said support structure supporting the substrate seals against the chamber to direct substantially all fluid flow within the chamber through the prosthesis to create a pressure drop.

14. The apparatus of claim 12, further comprising an inlet port and an outlet port located on opposite sides of said support structure on said at least one wall, said ports allowing fluid flow in and through said chamber.

15. The apparatus of claim 1, wherein said pressure creating means comprises a pressure plate, said pressure plate contacting and applying pressure to an exterior surface of said at least one wall of said chamber.

16. The apparatus of claim 1, wherein said pressure creating means comprises at least one roller, said at least one roller contacting and applying pressure to an exterior surface of said at least one wall of said chamber.

17. The apparatus of claim 1, wherein said chamber includes a first and a second port for flow of the fluid media therethrough.

18. The apparatus of claim 17, wherein said means for alternatingly creating a pressure differential within the chamber acting on the substrate includes a pump in fluid communication with said chamber.

19. The apparatus of claim 18, further comprising a supply of fluid media in communication with the pump.

20. The apparatus of claim 18, wherein said pump comprises a reversible pump.

21. The apparatus of claim 18, wherein said pump comprises a uni-directional pump.

22. The apparatus of claim 21, wherein said first port of said chamber is larger in diameter than said second port for creating a pressure drop at said second port when fluid media flows through said chamber from said film port to said second port.

23. The apparatus of claim 1, wherein said tissue is a cartilage prosthesis.

24. A method for seeding and culturing tissue in a chamber defined by at least one wall, comprising:
   disposing within the chamber a porous substrate configured and dimensioned to seal with the chamber, said substrate designed to facilitate three-dimensional tissue growth on said substrate and comprising a three-dimensional framework having interstitial spaces bridgeable by cells;
   exposing the substrate in the chamber to a flow of fluid media for seeding and culturing; and
   alternatingly creating a pressure differential across the substrate during seeding and culturing to force substantially all flow of the fluid media within the chamber through the substrate and facilitate exposure of the substrate to the fluid media.

25. The method of claim 24, wherein said step of creating pressure comprises:
   placing said substrate in a housing defining a chamber, said chamber being filled with fluid media for seeding and culturing; and
   applying a pressure differential to the fluid media across the substrate so that fluid media is forced therethrough.

26. The method of claim 25, wherein said step of applying pressure to the fluid media is accomplished through the use of a pump.

27. The method of claim 25, wherein said chamber is further defined by a piston and said step of applying pressure to the fluid media comprises actuating a piston so as to reduce the volume of the chamber.

28. The method of claim 25, wherein said housing comprises a bellows and said step of applying pressure to the fluid media comprises contracting said bellows.

29. The method of claim 25, wherein said step of applying pressure to the fluid media comprises applying a pressure plate to the housing.

30. The method of claim 25, wherein said step of applying pressure to the fluid media comprises applying a roller to the housing.

31. The method of claim 24, wherein said tissue is a cartilage prosthesis.

32. An apparatus for growing tissue, comprising:
   at least one wall defining a seeding and culturing chamber;
   a porous substrate disposed within said chamber configured and dimensioned to seal with the chamber such that the substrate divides the chamber into a first and a second portion, said substrate designed to facilitate three-dimensional tissue growth on said substrate and comprising a three-dimensional framework having interstitial spaces bridgeable by cells;
   means for alternatingly creating a high and a low pressure within the first portion relative to the second portion to create alternating flow of fluid media through said porous substrate between said portions;
   a support structure located within said chamber supporting the substrate and sealing with the chamber to direct substantially all fluid flow between said portions through the porous substrate.

33. The apparatus of claim 32, wherein the first portion includes a first port and the second portion includes a second port for flow of the fluid media therethrough.

34. The apparatus of claim 33, wherein said means for alternatingly creating a high and low pressure within the first portion of the chamber includes a pump in fluid communication said first port.

35. The apparatus of claim 34, further comprising a supply of fluid media in communication with the pump.

36. The apparatus of claim 34, wherein said pump comprises a reversible pump.

37. The apparatus of claim 34, wherein said pump comprises a unidirectional pump.

38. The apparatus of claim 37, wherein said first port of said chamber is larger in diameter than said second port for creating a pressure drop at said second port when fluid media flows through said chamber from said first port to said second port.

39. The apparatus of claim 32, wherein said tissue is cartilage tissue.

40. An apparatus for seeding and culturing a porous prosthesis within fluid media, comprising:
   at least one wall defining a chamber for seeding and culturing the prosthesis, said chamber including a first and a second port for flow of the fluid media therethrough, wherein said first port of said chamber is larger in diameter than said second port for creating a pressure drop at said second port when fluid media flows through said chamber from said first port to said second port;

a support structure located within said chamber configured and dimensioned to support the prosthesis such that the prosthesis seals with the chamber to direct substantially all fluid flow within the chamber through the prosthesis;

a unidirectional pump in fluid communication with the chamber for alternatingly creating a high and low pressure within the chamber acting on the prosthesis; and a supply of fluid media in communication with the pump.

41. The apparatus of claim 40, further comprising the porous prosthesis, said prosthesis disposed within said chamber and supported within said chamber by said support structure such that the prosthesis seals with the chamber to direct substantially all fluid flow within the chamber through the prosthesis.

42. The apparatus of claim 41, wherein said prosthesis is designed to facilitate three-dimensional tissue growth on said prosthesis.

43. The apparatus of claim 42, wherein said prosthesis comprises a three-dimensional framework having interstitial spaces bridgeable by cells.

* * * * *